United States Patent
Linko et al.

(10) Patent No.: US 10,300,168 B2
(45) Date of Patent: May 28, 2019

(54) POLYSACCHARIDE SOFT TISSUE FILLERS WITH IMPROVED PERSISTENCE

(71) Applicant: MERZ PHARMA GMBH & CO. KGAA, Frankfurt am Main (DE)

(72) Inventors: Alexander Linko, Frankfurt am Main (DE); Andreas Krause, Frankfurt am Main (DE); Franck Villain, Paris (FR)

(73) Assignee: MERZ PHARMA GMBH & CO. KGAA, Frankfurt am Mein (DE)

( * ) Notice: Subject to any disclaimer, the term of this patent is extended or adjusted under 35 U.S.C. 154(b) by 0 days.

(21) Appl. No.: 15/129,876

(22) PCT Filed: Mar. 31, 2015

(86) PCT No.: PCT/EP2015/000701
§ 371 (c)(1),
(2) Date: Sep. 28, 2016

(87) PCT Pub. No.: WO2015/149941
PCT Pub. Date: Oct. 8, 2015

(65) Prior Publication Data
US 2017/0143870 A1    May 25, 2017

(30) Foreign Application Priority Data
Apr. 1, 2014  (EP) .................... 14001213

(51) Int. Cl.
*A61L 27/20* (2006.01)
*A61L 27/26* (2006.01)
*A61L 27/50* (2006.01)
*A61L 27/52* (2006.01)
*A61K 31/737* (2006.01)
*A61K 31/738* (2006.01)
*A61P 17/00* (2006.01)

(52) U.S. Cl.
CPC ............... *A61L 27/20* (2013.01); *A61L 27/26* (2013.01); *A61L 27/50* (2013.01); *A61L 27/52* (2013.01); *A61L 2400/06* (2013.01); *A61L 2430/34* (2013.01)

(58) Field of Classification Search
None
See application file for complete search history.

(56) References Cited

U.S. PATENT DOCUMENTS

| 8,450,475 | B2 | 5/2013 | Lebreton | |
|---|---|---|---|---|
| 2005/0187185 | A1* | 8/2005 | Reinmuller | A61K 47/36 514/54 |
| 2008/0226690 | A1* | 9/2008 | DeAngelis | C07H 5/04 424/423 |
| 2013/0060230 | A1* | 3/2013 | Capistron | A61K 8/24 604/506 |
| 2013/0102563 | A1* | 4/2013 | Lebreton | A61K 8/735 514/54 |

FOREIGN PATENT DOCUMENTS

| WO | 2009056602 A1 | 5/2009 |
|---|---|---|
| WO | 2013149161 A1 | 10/2013 |

OTHER PUBLICATIONS

International Search Report dated Jul. 15, 2015 in counterpart application No. PCT/EP2015/000701.
European Search Report completed Dec. 18, 2014 in counterpart application No. EP 14001213.

\* cited by examiner

*Primary Examiner* — Abigail Vanhorn
(74) *Attorney, Agent, or Firm* — McBee Moore Woodward & Vanik IP, LLC

(57) ABSTRACT

The present invention relates to polysaccharide soft tissue fillers comprising heparosan and processes for their preparation. The polysaccharide soft tissue fillers of the present invention are advantageously used in therapeutic or cosmetic applications such as for the filling of wrinkles.

22 Claims, No Drawings

POLYSACCHARIDE SOFT TISSUE FILLERS WITH IMPROVED PERSISTENCE

CROSS REFERENCE TO RELATED APPLICATIONS

This application is a § 371 National Stage Application of PCT/EP2015/000701, filed 31 Mar. 2015, which claims priority to EP 14001213.9 filed 1 Apr. 2014.

FIELD OF THE INVENTION

The present invention relates to polysaccharide soft tissue fillers comprising heparosan and processes for their preparation. The present invention also relates to therapeutic and cosmetic uses of these polysaccharide soft tissue fillers.

BACKGROUND OF THE INVENTION

The replacement or filling of a biological tissue or the increase of tissue volume can be necessary or desirable in many therapeutic and cosmetic applications. One way to achieve this is the introduction of viscoelastic products based on permanent or biodegradable materials into the biological tissue.

With regard to therapeutic applications, the viscoelastic products can be used for increasing the volume of certain tissues, for example of the sphincter, the urethra or the vocal cords. In case of cosmetic applications, potential applications include filling of wrinkles, masking scars or augmenting the volume of the lips. The injection of viscoelastic products is a simple non-invasive method with fewer risks than aesthetic surgery.

The use of viscoelastic products based on permanent materials offers the advantage of a long residence time in the tissue, but has major drawbacks. For example, the injection of silicone is associated with undesirable long-term effects characterized by the appearance of nodules and ulcers of the skin. Further, the injection of particles in solution or in a biopolymer matrix entails the risk of unwanted inflammatory reactions, and the migration of synthetic fragments may even lead to the appearance of granulomas.

Therefore, viscoelastic products based on crosslinked biodegradable biopolymers in the form of gels are increasingly used in therapeutic treatments and in the dermo-cosmetic field. The biodegradable polymers used in these gels are typically naturally occurring polymers that can be resorbed over time in the tissue where they have been injected. A large majority of the commercial gel products, in particular of dermal fillers, employ crosslinked hyaluronic acid (HA) as a preferred biodegradable polymer. Different crosslinking agents such as DVS (divinyl sulfone), DEO (diepoxyoctane) and BDDE (1,4-butanediol diglycidyl ether) can be used.

Biodegradable biopolymer gels are commonly classified in two different types, the "single-phase" (or "monophasic") gels and the "two-phase" (or "biphasic") gels. The biphasic gels comprise a material that consists of one or more crosslinked biopolymers (e.g., sodium hyaluronate) dispersed within a fluid phase or in a non-crosslinked biopolymer-based solution (see, e.g., EP 0 466 300 B1). The crosslinked biopolymer material degrades slowly by surface degradation, whereas the non-crosslinked biopolymer (e.g., sodium hyaluronate) degrades very quickly. As a result, when an increase in tissue volume is desired, numerous after-treatments are necessary after the first injection, which reduces the user's quality of life. Examples of commercially available biphasic, biodegradable gels include, among others, the dermal fillers Hylaform®, Restylane®, and Perlane®.

The monophasic gels are also based on one or more crosslinked biodegradable biopolymers (e.g., sodium hyaluronate), but comprise only a single phase, meaning it is a gel with no visible particles. In view of the crosslinked nature, these gels undergo slow surface degradation. Such monophasic viscoelastic gels have been described, for example, in WO 2008/068297 A1, U.S. Pat. No. 8,450,475 B2, U.S. Pat. No. 8,455,465 B2, U.S. Pat. No. 7,741,476 B2, and U.S. Pat. No. 8,052,990 B2. Commercial monophasic HA gels include, among others, Juvederm®, Teosyal®, Glytone®, and the monophasic, double-crosslinked (polydensified) HA gels marketed under the brand names Belotero®, Esthélis®, Fortélis® Extra, and Modélis® Shape.

An improved persistence, i.e. a longer residence time in the human body, of fillers is thought to be beneficial due to the expected reduction in the number and frequency of treatments required to obtain a satisfactory result. The cross-linking significantly improves the persistence. However, the injection of a highly crosslinked polymer is more difficult which is an undesirable characteristic. In addition, upon injection of the gel, the non-crosslinked sites of the polymer become more prone to biochemical and enzymatic attacks, which promotes degradation of the gel.

Therefore, additional attempts have been made to further increase the persistence of biopolymer-based fillers. For example, it was proposed to incorporate particles made from crosslinked HA or (meth)acrylic acid into a crosslinked HA polymer matrix (see, e.g., WO 00/01428 A1 and US 2010/0028435 A1). This approach, however, is associated with the risk of unwanted inflammatory reactions and even granulomas. In addition, WO 2013/149161 A1 discloses the production of high molecular weight heparosan, a polymer that is similar to HA but is more resistant against degradation, and proposes its use as a biomaterial composition for, among others, tissue augmentation.

OBJECT OF THE INVENTION

In view of the above, the object of the present invention is to provide a soft tissue filler that has a long persistence, is easily injectable and has a strong capacity to create an increase in tissue volume.

SUMMARY OF THE INVENTION

The above object is solved by the provision of injectable soft tissue filler compositions in the form of a crosslinked gel, comprising heparosan and hyaluronic acid (HA), or one of their salts. These new types of soft tissue fillers have a long residence time in the human body (i.e. long persistence), can be easily injected through a needle and have an excellent ability to create volume.

In a first aspect, the present invention provides a first injectable soft tissue filler composition in the form of a gel, comprising heparosan and hyaluronic acid (HA), or one of their salts, crosslinked with a crosslinking agent, preferably 1,4-butanediol diglycidyl ether (BDDE), to form a crosslinked HA-heparosan matrix. Preferably, this first composition in the form of a gel is prepared by crosslinking a mixture of heparosan, or one of its salts, and HA, or one of its salts, using BDDE as crosslinking agent to form a crosslinked HA-heparosan matrix comprised of heparosan and HA polymers that are inter-molecularly (i.e. between HA molecules, heparosan molecules, or HA and heparosan molecules) or intra-molecularly crosslinked by BDDE.

In another aspect, the present invention provides a second injectable soft tissue filler composition in the form of a gel, comprising a mixture of (i) a pre-formed gel of BDDE-crosslinked hyaluronic acid (HA), or one of its salts, and (ii) a pre-formed gel of BDDE-crosslinked heparosan, or one of its salts.

In a further aspect, the present invention provides a third injectable soft tissue filler composition in the form of a gel, comprising a double-crosslinked hyaluronic acid (HA)-heparosan matrix prepared by (a) BDDE-crosslinking heparosan, or one of its salts, to form a crosslinked heparosan gel, mixing HA, or one of its salts, with the crosslinked heparosan gel, and BDDE-crosslinking the HA, or one of its salts, and the crosslinked heparosan gel to obtain said double-crosslinked HA-heparosan matrix, or (b) BDDE-crosslinking HA, or one of its salts, to form a crosslinked HA gel, mixing heparosan, or one of its salts, with the crosslinked HA gel, and BDDE-crosslinking the heparosan, or one of its salts, and the crosslinked HA gel to obtain said double-crosslinked HA-heparosan matrix.

In a still further aspect, the present invention provides a fourth injectable soft tissue filler composition in the form of a gel, comprising a triple-crosslinked hyaluronic acid (HA)-heparosan matrix prepared by BDDE-crosslinking heparosan, or one of its salts, to form a crosslinked heparosan gel, BDDE-crosslinking HA, or one of its salts, to form a crosslinked HA gel, mixing the crosslinked heparosan gel with the crosslinked HA gel, and BDDE-crosslinking the mixture of the crosslinked heparosan gel and the crosslinked HA gel to obtain said triple-crosslinked HA-heparosan matrix.

In yet another aspect, the present invention provides a fifth injectable soft tissue filler composition comprising a crosslinked, preferably BDDE-crosslinked, heparosan matrix and calcium hydroxyapatite.

In still another aspect, there is provided a kit comprising a syringe containing an injectable soft tissue filler of the present invention.

In a yet further aspect, the present invention provides processes for the preparation of the first to fifth injectable soft tissue filler compositions of the present invention. In particular, there are provided:
(i) a process for the preparation of the first injectable soft tissue filler composition of the present invention, comprising the steps of:
  (a) providing an aqueous mixture comprising hyaluronic acid (HA), heparosan and a crosslinking agent, preferably 1,4-butanediol diglycidyl ether (BDDE), and
  (b) crosslinking the mixture of (a), preferably using BDDE as crosslinking agent, to obtain a crosslinked HA-heparosan matrix, and
(ii) a process for the preparation of the second injectable soft tissue filler composition of the present invention, comprising the steps of:
  (i) providing an aqueous mixture comprising hyaluronic acid (HA), or one of its salts, and 1,4-butanediol diglycidyl ether (BDDE),
  (ii) crosslinking the mixture of (i) using BDDE as crosslinking agent to obtain a crosslinked HA gel,
  (iii) providing an aqueous mixture comprising heparosan, or one of its salts, and 1,4-butanediol diglycidyl ether (BDDE),
  (iv) crosslinking the mixture of (iii) using BDDE as crosslinking agent to obtain a crosslinked heparosan gel, and
  (v) mixing the crosslinked HA gel of step (ii) and the crosslinked heparosan gel of step (iv); or
(iii) a process for the preparation of the third injectable soft tissue filler composition of the present invention, comprising the steps of:
  (a') providing an aqueous mixture comprising heparosan, or one of its salts, and 1,4-butanediol diglycidyl ether (BDDE),
  (b') crosslinking the mixture of (a') using BDDE as crosslinking agent to obtain a crosslinked heparosan gel,
  (c') mixing HA, or one of its salts, and, optionally, BDDE with the crosslinked heparosan gel, and
  (d') crosslinking the mixture of (c') using BDDE as crosslinking agent to obtain a double-crosslinked HA-heparosan matrix,
or comprising the following steps:
  (a") providing an aqueous mixture comprising HA, or one of its salts, and 1,4-butanediol diglycidyl ether (BDDE),
  (b") crosslinking the mixture of (a") using BDDE as crosslinking agent to obtain a crosslinked HA gel,
  (c") mixing heparosan, or one of its salts, and, optionally, BDDE with the crosslinked HA gel, and
  (d") crosslinking the mixture of (c") using BDDE as crosslinking agent to obtain a double-crosslinked HA-heparosan matrix; or
(iv) a process for the preparation of the fourth injectable soft tissue filler composition of the present invention, comprising the steps of:
  (1) providing an aqueous mixture comprising HA, or one of its salts, and 1,4 butanediol diglycidyl ether (BDDE),
  (2) crosslinking the mixture of (1) using BDDE as crosslinking agent to obtain a crosslinked HA gel,
  (3) providing an aqueous mixture comprising heparosan, or one of its salts, and 1,4 butanediol diglycidyl ether (BDDE),
  (4) crosslinking the mixture of (3) using BDDE as crosslinking agent to obtain a crosslinked heparosan gel,
  (5) mixing the crosslinked HA gel of (2) and the crosslinked heparosan gel of (4) and, optionally, BDDE, and
  (6) crosslinking the mixture of (5) using BDDE as crosslinking agent to obtain a triple-crosslinked HA-heparosan matrix; or
(v) a process for the preparation of the fifth injectable soft tissue filler composition of the present invention, comprising the steps of:
  (A) providing an aqueous mixture comprising heparosan, or one of its salts, and a crosslinking agent, preferably 1,4-butanediol diglycidyl ether (BDDE),
  (B) crosslinking the heparosan, or one of its salts, preferably using BDDE as crosslinking agent, to obtain a crosslinked heparosan matrix, and
  (C) adding calcium hydroxyapatite.

In still another aspect, the present invention relates to the use the injectable soft tissue filler compositions of the present invention, or of the kit of the present invention, for replacing or filling of a biological tissue or increasing the volume of said biological tissue. Particularly advantageously, the filler compositions are used in the dermocosmetic field for reducing wrinkles or lines of the skin.

Preferred embodiments of the present invention are set forth in the appended dependent claims.

DETAILED DESCRIPTION OF THE INVENTION

The inventors of the present invention have unexpectedly found that crosslinking a polysaccharide, such as hyaluronic acid (HA), with heparosan results in a gel exhibiting a long residence time in the body, while at the same time exhibiting favorable properties for use as a soft tissue filler in, for example, dermo-cosmetic applications.

Heparosan (HEP) is a biopolymer belonging to the glycosaminoglycan (GAG) family of polysaccharides. In humans, it is an intermediate product in the biosynthesis of heparin and heparin sulfate. The structure of heparosan is highly similar to that of hyaluronan (HA) since it has the same monosaccharide component sugars as hyaluronan and differs from HA only in that the β-(1,3) glycosidic bond between the glucuronic acid (GlcUA) and the N-acetylglucosamine (GlcNAc) in HA is replaced by a β-(1,4) glycosidic bond in HEP and in that the β-(1,4) glycosidic bond between N-acetylglucosamine (GlcNAc) and the glucuronic acid (GlcUA) in HA is replaced by a α-(1,4) glycosidic bond in HEP:

GlcUA-β-(1-4)-[GlcNAc-α-(1-4)-GlcUA-β-(1-4)]$_n$-GlcNAc HEP

GlcUA-β-(1-3)-[GlcNAc-β-(1-4)-GlcUA-β-(1-3)]$_n$-GlcNAc HA

A key characteristic of heparosan is its excellent biocompatibility. Heparan carries a high number of negative charges and hydroxyl groups and is therefore highly hydrophilic, which increases tissue compatibility. Furthermore, due to the fact that heparosan polymers, even after modification, still comprise stretches that occur in natural heparan sulfate and heparin polymers, heparosan is non-immunogenic (e.g., does not induce antibodies). Moreover, due to the structural similarity between heparosan and hyaluronan, the same chemical modifications, including crosslinking, as that known for hyaluronan can be made on the functional groups.

In addition, no extracellular hydrolytic enzymes are produced in humans that specifically degrade heparosan, resulting in a prolonged persistence in the body as compared to hyaluronic acid. Also, no accumulation of potentially harmful breakdown products occurs. The term "persistence", as used herein, refers to the ability of the soft tissue filler to withstand in vivo degradation for an extended period of time. Therefore the term persistence is synonymously used to refer to "residence time (in the body)" or "life time".

The injectable soft tissue filler of the present invention provides a number of advantages over known fillers, including excellent biocompatibility, improved persistence, low extrusion force (ease of injectability), high moisture retention, no immunogenicity, and safe absorption by the body, while maintain desirable mechanical and rheological properties for use as a soft tissue filler.

In a first aspect, the present invention relates to a first injectable soft tissue filler composition in the form of a gel, comprising heparosan and hyaluronic acid (HA), or one of their salts, crosslinked with 1,4-butanediol diglycidyl ether (BDDE), to form a crosslinked HA-heparosan matrix.

The term "soft tissue filler composition", as used herein, is intended to mean a composition that is used or suitable for use as a soft tissue filler. A "soft tissue filler" within the meaning of the present invention refers to a material designed to add volume to areas of soft tissue deficiency. The term "soft tissue" generally relates to tissues that connect, support, or surround other structures and organs of the body. In the present invention, soft tissue includes, for example, muscles, tendons (bands of fiber that connect muscles to bones), fibrous tissues, fat, blood vessels, nerves, and synovial tissues (tissues around joints). In the context of the present invention, the soft tissue filler is preferably a dermal filler. Applications of soft tissue fillers include, but are not limited to dermo-cosmetic applications, such as adding fullness to the lips, augmenting cheeks, treating skin lines or wrinkles, or therapeutic applications, such as increasing the volume of other tissues in need thereof such as the sphincter, the urethra or the vocal cords.

According to the present invention, the injectable soft tissue filler composition is a gel. The term "gel", as used herein, generally refers to a material having fluidity at room temperature between that of a liquid and solid. In addition, the term "gel" is intended to mean a material capable of absorbing water (i.e. a "hydrogel"), typically in an amount of at least 90 wt. % based on the total weight of the gel (without the weight of optionally present particles (i.e. calcium hydroxyapatite particles)). Within the present invention, the injectable soft tissue filler composition generally comprises a physiologically acceptable carrier fluid, preferably an apyrogenic isotonic buffer, more preferably a physiological saline solution.

In accordance with the present invention, polysaccharides are used to form a "matrix". As used herein, the term "matrix" is intended to mean a network of polysaccharides, either crosslinked or non-crosslinked, in the form of a solution or gel. As used herein, the term "hyaluronic acid" or "HA" means hyaluronic acid, hyaluronate, and any hyaluronate salt such as sodium hyaluronate. Likewise, the term "heparosan", as used herein includes any salts thereof.

Furthermore, the soft tissue filler composition of the present invention is "injectable". This means that the soft tissue filler composition is suitable for injection into the skin or other tissue in order to bring the soft tissue filler composition to the desired target site. An "injectable" composition within the meaning of the present invention can be dispensed from syringes under normal conditions under normal pressure.

Generally, the soft tissue fillers of the present invention are, unless otherwise stated, not limited to a particular type of gel and include injectable monophasic and biphasic gels, injectable gels comprising a crosslinked matrix with integrated or covalently co-crosslinked biopolymer particles or with other particles dispersed therein, polydensified or double-crosslinked gels (i.e. gels characterized by a variation of the degree of crosslinking within the gel), triple-crosslinked gels and non-crosslinked gels. The soft tissue filler of the present invention may be a monophasic gel made analogously to the HA gel described in US 2010/0316683 A1, which is incorporated herein by reference. Furthermore, the soft tissue filler of the present invention may be prepared in accordance with the method disclosed in WO 2013/185934 A1, which is also incorporated herein by reference. The manufacturing of polydensified gels (i.e. double-crosslinked gels) is for example described in EP 1 711 552 B1, which is also incorporated herein by reference.

In the case of crosslinked gels, the soft tissue filler of the present invention is preferably an injectable gel having simultaneously the characteristics of being monophasic, cohesive, and long-lasting. The term "cohesive", as used herein, means a tendency of the gel to regroup and not to spread out or break apart. The cohesive character of the gel thus contributes to obtaining a high compatibility and long persistence in the soft tissue.

The present invention further relates to a second, third, fourth and fifth soft tissue filler composition in the form of a gel, which are described below. It goes without saying that the explanations and definitions provided above in relation to the first injectable soft tissue filler composition (e.g., the definitions of the terms persistence, soft tissue filler composition, soft tissue filler, soft tissue, filler, gel, hydrogel, matrix, hyaluronic acid, heparosan, injectable, the types of gel, cohesive, etc.) equally apply to the second, third, fourth and fifth (explained further below) injectable soft tissue filler composition of the present invention.

According to the present invention, there is further provided a second injectable soft tissue filler composition in the form of a gel, comprising a mixture of (i) a pre-formed gel of BDDE-crosslinked hyaluronic acid (HA), or one of its salts, and (ii) a pre-formed gel of BDDE-crosslinked heparosan, or one of its salts. This gel composition may be obtained by first preparing (i) and (ii), and then physically mixing (i) and (ii) in a desired weight ratio in accordance with techniques known to those skilled in the art.

Preferably, the second injectable soft tissue filler composition is obtainable by a process of the invention as described herein. The weight ratio of (i):(ii) is preferably from 0.1:99.9 to 99.9:0.1, more preferably from 1.0:99.0 to 99.9:1.0, particularly preferred from 5:95 to 95:5, from 10:90 to 90:10 or from 20:80 to 80:20, and most preferably from 30:70 to 70:30 or from 40:60 to 60:40.

Furthermore, the present invention relates to a third injectable soft tissue filler composition in the form of a gel, comprising a double-crosslinked hyaluronic acid (HA)-heparosan matrix prepared by (a) BDDE-crosslinking heparosan or one of its salts, to form a crosslinked heparosan gel, mixing HA, or one of its salts, with the crosslinked heparosan gel, and BDDE-crosslinking the HA, or one of its salts, and the crosslinked heparosan gel to obtain said double-crosslinked HA-heparosan matrix, or (b) BDDE-crosslinking HA, or one of its salts, to form a crosslinked HA gel, mixing heparosan, or one of its salts, with the crosslinked HA gel, and BDDE-crosslinking the heparosan, or one of its salts, and the crosslinked HA gel to obtain said double-crosslinked HA-heparosan matrix.

Preferably, the third injectable soft tissue filler composition is obtainable by a process of the invention as described herein. The second crosslinking may be carried out using BDDE remaining in the first crosslinking reaction mixture (e.g., by adding the HA or heparosan used for the second crosslinking to the first crosslinking reaction mixture comprising the crosslinked first polymer (i.e. HA or heparosan)). Typically, the dilution of the reaction mixture that comes along with the addition of the second polymer (i.e. the HA or heparosan to be crosslinked in the second crosslinking step) results in a varying degree (e.g., lower degree) of crosslinking in the gel (heterogeneous crosslinking).

Alternatively a supplemental quantity of BDDE is added after the first crosslinking step to effect the second crosslinking. Typically, the added quantity is (substantially) less than the quantity added for the first (or initial) crosslinking. The double crosslinked gel according to the present invention is advantageously characterized by facilitated injectability, long remanence in vivo and excellent viscoelastic properties.

The term "polydensified", as used herein, refers to a gel that is characterized by a variation of the degree of crosslinking within the gel or, to put it in other words, a "polydensified" gel has (at least) two different density levels with denser parts (higher degree of crosslinking) and less dens parts (lower degree of crosslinking). Generally, the double-crosslinked or triple-crosslinked gels of the present invention, e.g. a double-crosslinked gel prepared by a first crosslinking reaction to crosslink first polysaccharide(s), followed by a second crosslinking reaction to crosslink second polysaccharide(s), are such polydensified gels. Further, the polydensified gels of the present invention are typically monophasic and exhibit a high cohesivity. The double-crosslinking process (dynamic cross-linking technology) is known in the art and is described, for example, in EP 1 711 552 B1, which is incorporated herein by reference.

Still further, the present invention relates to a fourth injectable soft tissue filler composition in the form of a gel, comprising a triple-crosslinked hyaluronic acid (HA)-heparosan matrix prepared by BDDE-crosslinking heparosan, or one of its salts, to form a crosslinked heparosan gel, BDDE-crosslinking HA, or one of its salts, to form a crosslinked HA gel, mixing the crosslinked heparosan gel with the crosslinked HA gel, and BDDE-crosslinking the mixture of the crosslinked heparosan gel and the crosslinked HA gel to obtain said triple-crosslinked HA-heparosan matrix.

As explained above with respect to the double-crosslinked gel of the present invention, the residual BDDE present in the (first and/or second) crosslinking reaction mixture may be used for effecting a further (third) crosslinking reaction or optionally a supplemental quantity of BDDE may be added. The comments provided above with regard to the third composition similarly apply to the fourth composition.

In the following, particular embodiments of the different injectable soft tissue filler compositions of the present invention are described (the fifth injectable soft tissue filler composition is described further below). The explanations, definitions and further features of these compositions described below equally apply to the first, second, third, fourth and fifth injectable soft tissue filler composition of the present invention without the need of an explicit mention, unless otherwise stated. Furthermore, it is to be understood that all embodiments described in the context of compositions or kits of the invention equally apply to methods of treatment, uses and vice versa. Thus, the mentioning of a particular embodiment in the context of a composition or a kit, method of treatment or use describes this embodiment for all these kinds of subject matter.

The weight ratio of heparosan to HA in the crosslinked HA-heparosan matrix of the first, third or fourth soft tissue filler of the present invention may range from about 0.1:99.9 to 99.9 to 0.1 or from about 1:99 to about 99:1, preferably from about 50:50 to about 1:99, more preferably from about 25:75 to about 1:99, yet more preferably from about 10:90 to about 1:99, particularly preferably from about 5:95 to about 1:99, and most preferably from about 3:97 to about 1:99.

The crosslinked HA-heparosan matrix of the injectable soft tissue filler compositions of the present invention has preferably a degree of modification, expressed as the ratio of the sum of mono- and double-linked BDDE-crosslinkers to the sum of HA and heparosan disaccharide units, of about 0.5% to about 25%, more preferably from about 2.0% to about 20%, even more preferably from about 3.0% to about 15%, yet more preferably from about 4.0% to about 12%, still more preferably from about 5.0% to about 10.0%, particularly preferably from about 6.0% to about 9.0%, and most preferably from about 7.0% to about 8.0%.

The degree of modification can be determined by NMR in accordance with methods known in the art (Edsman et al., Gel Properties of Hyaluronic Acid Dermal Fillers, Dermatol. Surg. 2012, 38:1170-1179; Guarise et al., SEC determination of cross-link efficiency in hyaluronan fillers, Carbohydrate Polymers 2012, 88:428-434; Kenne et al., Modification and cross-linking parameters in hyaluronic acid hydrogels—Definitions and analytical methods, Carbohydrate Polymers 2013, 91:410-418).

In brief, the dialyzed and sterilized gels are degraded before conducting the NMR measurement. The degradation can be performed by chondroitinase AC (Edsman et al., supra; Kenne et al., supra), NaOH (Guarise et al., supra), addition of hyaluronidase (e.g., 150 U ovine hyaluronidase to 1 g of gel) or by incubation at 90° C. for at least 35 h. The obtained solutions are then lyophilized, dissolved in $D_2O$, and well homogenized.

The NMR measurement can be performed at, e.g., 500 MHz, at a pulse of 20 degree with several repetitions at ambient temperature to receive a spectrum with appropriate resolution. In accordance with the literature, the degree of modification (MoD) is assessed by calculating the ratio of the N-acetyl signals of HA to the methylene signals of BDDE. For N-acetyl of HA, the critical signals are located at about 2.0 ppm and at about 1.6 ppm for BDDE when solubilized in $D_2O$. In order to calculate the degree of modification, the integral values were identified and the ratio of protons of 3H of N-acetyl ($CH_3$) to 4H of methylene ($CH_2CH_2$) needs to be taken in account, in accordance with the literature (Edsman et al., supra, and Kenne et al., supra).

The molecular weight of the heparosan polymers used for the preparation of the soft tissue fillers of the present invention may range from about $0.5 \times 10^5$ Da to about $6.8 \times 10^6$ Da, preferably from about $1.0 \times 10^5$ Da to about $5.0 \times 10^6$ Da, and more preferably from about $1.0 \times 10^5$ Da to about $3.5 \times 10^6$ Da. In another preferred embodiment, the molecular weight of the heparosan polymer is from about $0.5 \times 10^5$ Da to about $1.0 \times 10^6$ Da or less, more preferably from about $2.0 \times 10^5$ Da to about $8.0 \times 10^5$ Da, and most preferably from about $3.0 \times 10^5$ Da to about $7.0 \times 10^5$ Da.

The molecular weight of the HA polymers used for the preparation of the soft tissue fillers of the present invention is not particularly limited but is typically in the range of from about $1.0 \times 10^5$ Da to about $5.0 \times 10^6$ Da, preferably in the range from about $3.0 \times 10^5$ Da to about $3.0 \times 10^6$ Da, and more preferably in the range of from about $5.0 \times 10^5$ Da to about $2.5 \times 10^6$ Da.

Various methods can be applied herein to determine the molecular weight of HA, such as intrinsic viscosity (e.g., according to Chinese Pharmacopoeia, $2^{nd}$ revision, 2006), capillary electrophoresis (CE) (e.g., according to Kinoshita et al., Biomed. Chromatogr., 2002, 16:141-45), high performance gel permeation chromatography (HPGPC) (e.g., according to Kim et al., Food Chem., 2008, 109: 63-770), and multi-angle laser light scattering combined with size-exclusion chromatography (SEC-MALLS) (e.g., in accordance to Hokputsa et al., Eur. Biophys. J. Biophys. Lett., 2003, 32:450-456).

The degree of modification and, to a much lesser extent, the polysaccharide molecular weight have an impact on the degradation stability and, thus, allow to adjust the persistence of the injectable soft tissue filler of the present invention. A higher molecular weight of the used polysaccharides, e.g. of HA and/or heparosan, generally results in a longer residence time of the soft tissue filler in the body. With regard to the degree of crosslinking the following applies: the higher the degree of crosslinking, the longer the residence time in the body.

In a preferred embodiment of the present invention, the HA of the injectable soft tissue filler compositions of the present invention comprises a first HA having a first molecular weight and a second HA having a second molecular weight that is different to the first molecular weight.

Preferably, the HA comprises a first HA having a first molecular weight in the range of from about $0.5-1.0 \times 10^5$ Da to less than about $1.0 \times 10^6$ Da and a second HA having a second molecular weight in the range of from about $1.0 \times 10^6$ Da to about $5.0 \times 10^6$ Da, more preferably a first HA having a first molecular weight in the range of from about $1.0 \times 10^5$ Da to about $9.0 \times 10^5$ Da and a second HA having a second molecular weight in the range of from about $1.1 \times 10^6$ Da to about $4.0 \times 10^6$ Da, and most preferably a first HA having a first molecular weight in the range of from about $2.0 \times 10^5$ Da to about $6.0 \times 10^5$ Da and a second HA having a second molecular weight in the range of from about $1.3 \times 10^6$ Da to about $2.0 \times 10^6$ Da.

The weight ratio of the first HA to the second HA in the injectable soft tissue filler compositions of the present invention is preferably from about 50:50 to about 99:1, more preferably from about 70:30 to about 95:5, and most preferably from about 85:15 to about 95:5.

In another preferred embodiment, the heparosan of the injectable soft tissue filler composition of the present invention comprises a first heparosan and a second heparosan characterized by having different molecular weights.

Preferably, the heparosan comprises a first heparosan having a first molecular weight in the range of from about $1.0 \times 10^5$ Da and $9.0 \times 10^5$ Da and a second heparosan having a second molecular weight in the range of from about $1.0 \times 10^6$ to $3.0 \times 10^6$ Da, more preferably a first heparosan having a first molecular weight in the range of from about $1.0 \times 10^5$ Da and $5.0 \times 10^5$ Da and a second heparosan having a second molecular weight in the range of from about $1.5 \times 10^6$ to $3.0 \times 10^6$ Da.

The weight ratio of the first heparosan to the second heparosan in the injectable soft tissue filler compositions of the present invention is preferably from about 50:50 to about 99:1, more preferably from about 70:30 to about 95:5, and most preferably from about 85:15 to about 95:5.

In a preferred embodiment, the injectable soft tissue filler compositions of the present invention further comprise non-crosslinked HA and/or non-crosslinked heparosan. The non-crosslinked polymers are added to the filler as a lubricant and help to make the final product flow and facilitate injection.

The non-crosslinked HA has preferably a molecular weight of from about $3.0 \times 10^5$ Da to about $3.0 \times 10^6$ Da, more preferably from about $8.0 \times 10^5$ Da to about $2.5 \times 10^6$ Da, and most preferably from about $1.0 \times 10^6$ Da to about $1.5 \times 10^6$ Da. The non-crosslinked heparosan has preferably a molecular weight of from about $1.0 \times 10^5$ Da to about $6.8 \times 10^6$ Da, more preferably from about $5.0 \times 10^5$ Da to about $5.0 \times 10^6$ Da, and most preferably from about $1.0 \times 10^6$ Da to about $3.5 \times 10^6$ Da.

The total amount of said non-crosslinked HA and/or said non-crosslinked heparosan is preferably from about 0.001 wt. % to about 50 wt. % or from about 0.01 wt. % to about 40 wt. % or from about 0.1 wt. % to about 35 wt. % or from about 1 wt. % to about 30 wt. %, more preferably from about 1 wt. % to about 20 wt. %, and most preferably from about 5 wt. % to about 20 wt. %, based on the total weight of the crosslinked and non-crosslinked heparosan and HA polymers present in the injectable soft tissue filler compositions.

Preferably, the injectable soft tissue filler compositions of the present invention contain no other non-crosslinked polymer than non-crosslinked HA. Also preferably, the injectable soft tissue filler compositions of the present invention do not contain any non-crosslinked polymers. In this context, the term "polymer", as used herein, refers to any natural or synthetic polymeric compound with repeating structural units, including polysaccharides such as HA and heparosan.

According to the present invention, the total concentration of the crosslinked and non-crosslinked heparosan and crosslinked and non-crosslinked HA polymers present in the injectable soft tissue filler compositions of the present invention is preferably from about 0.5 mg/ml to about 40 mg/ml, from about 1 mg/ml to about 40 mg/ml, from about 5 mg/ml to about 35 mg/ml or from about 10 mg/ml to about 35 mg/ml, more preferably from about 15 mg/ml to about 30 mg/ml, even more preferably from about 18 mg/ml to about 28 mg/ml, and most preferably from about 20 mg/ml to about 26 mg/ml. Further, in case the filler compositions contain non-crosslinked heparosan and/or non-crosslinked HA polymers, it is preferred that both the crosslinked HA-heparosan matrix as well as the added non-crosslinked heparosan and/or HA polymers have a concentration within the above-indicated ranges.

The present invention further contemplates the use of one or more additional polysaccharides other than HA and heparosan, preferably in an amount of less than 10 wt. %, based on the total weight of all polysaccharides contained in the injectable soft tissue filler compositions of the present invention. Desirably, the polymers are of natural origin. The use of polymer of natural origin permits better biocompatibility, which gives rise to less risk of inflammatory reactions. Examples of suitable additional polysaccharides include, but are not limited to, chondroitin sulfate, keratan, keratan sulfate, heparin, heparin sulfate, cellulose and its derivatives, chitosan, carrageenan, xanthan, and alginate, or one of their salts.

The additional polysaccharide(s) other than HA and heparosan are preferably all co-crosslinked with the hyaluronic acid and heparosan polymers of the HA-heparosan matrix. However, in less preferred embodiments, the additional polysaccharide(s) other than HA and heparosan may partly or fully be present in non-crosslinked form.

In a preferred embodiment, the injectable soft tissue filler compositions of the present invention do not contain any non-crosslinked and crosslinked polymers other than HA and heparosan.

The present invention yet further contemplates that the injectable soft tissue filler compositions of the present invention may comprises particles that typically have an average particle size of about 1 µm to about 1000 µm, in particular of about 10 µm to 200 µm. The particles are preferably integrated in the crosslinked HA-heparosan matrix of the injectable soft tissue filler compositions of the present invention. The particles may be crosslinked particles, in particular crosslinked HA particles.

Preferably, the particles are ceramic particles. A particularly suitable ceramic material for use herein is an apatite selected from hydroxyapatite, fluorapatite, and chlorapatite, or a mixture thereof. Preferably, the particles are calcium hydroxyapatite particles. The ceramic particles (e.g. calcium hydroxyapatite particles) are typically contained in the injectable soft tissue filler in an amount of from about 1 wt. % to about 65 wt. % or from about 5 wt. % to about 60 wt. %, in particular in an amount of from about 10 wt. % to about 50 wt. %, preferably in an amount of about 20 wt. % to about 40 wt. %. The size of the ceramic particles (e.g. of calcium hydroxyapatite particles) is preferably in the range of about 1 µm to about 1000 µm, more preferably in the range of about 10 µm to about 200 µm, and most preferably in the range of about 25 µm to about 50 µm. Furthermore, the ceramic particles have preferably a volume percent of about 5% to about 65%.

In a particularly preferred embodiment of the present invention, the above-described injectable soft tissue filler compositions of the present invention that contain ceramic particles, in particular calcium hydroxyapatite particles, further comprises glycerol and/or mannitol and/or lidocaine.

The present invention still further contemplates the inclusion of at least one active substance, for example one or more anesthetic agents, in the injectable soft tissue filler compositions described herein. The anesthetic agent is typically a local anesthetic such as lidocaine. Preferably, the lidocaine is comprised in the soft tissue filler of the present invention in a concentration of from about 0.05 wt. % to about 5.0 wt. %, more preferably from about 0.1 wt. % to about 2.0 wt. %, even more preferably from 0.1 wt. % to about 2.0 wt. %, still more preferably from 0.1 wt. % to about 1.0 wt. %, particularly preferably from about 0.1 wt. % to about 0.5 wt. %, and most preferably from about 0.2 wt. % to about 0.4 wt. %, based on the total weight of the injectable soft tissue filler composition.

In addition, the injectable soft tissue filler compositions of the present invention may optionally comprise one or more compounds selected from polyols, vitamins, amino acids, metals, minerals. Furthermore, the soft tissue filler of the present invention may also contain stem cells and/or growth factors and/or common additives (e.g. pH modifiers and osmolality adjusters).

Exemplary polyols for use herein include, but are not limited to mannitol, glycerol, propylene glycol, sorbitol, erythritol, xylitol, lactitol, maltitol and glucose. Particularly suitable for use herein is mannitol and glycerol. The total concentration of polyol(s) is generally between about 0.01 mg/ml and about 50.0 mg/ml, preferably between about 0.5 mg/ml and about 20.0 mg/ml, more preferably between about 1.0 mg/ml and about 5.0 mg/ml. The polyols may be used as antioxidizing agents, which improve the gel's ability to withstand in vivo degradation.

Suitable vitamins include vitamin C, vitamin E and vitamins of the B group, i.e. one or more of $B_1$, $B_2$, $B_3$, $B_5$, $B_6$, $B_7$, $B_9$ and $B_{12}$ vitamins. The concentration of vitamin C or of vitamin E is preferably from about 0.01 mg/ml to about 10.0 mg/ml, more preferably from about 0.1 mg/ml to about 5.0 mg/ml, and the total concentration of the vitamins of the B group is preferably from about 0.01 mg/ml to about 10.0 mg/ml, more preferably from about 0.1 mg/ml to about 5.0 mg/ml. The vitamins may be present to stimulate and maintain cellular metabolism and, thus, to promote collagen production. Particularly preferred for use here is vitamin C, vitamin E and vitamin $B_6$.

In accordance with the present invention, the injectable soft tissue filler compositions have generally an elastic modulus G' at a crossover frequency (f) of 1 Hz of from about 20 Pa to 1000 Pa, preferably from about 100 Pa to about 500 Pa, more preferably from about 250 Pa to about 500 Pa, for filler compositions without particles (e.g., ceramic particles like calcium hydroxyapatite). In case of filler compositions comprising particles (e.g., ceramic particles like calcium hydroxyapatite particles), the elastic modulus G' at a crossover frequency (f) of 1 Hz may be in the range of from about 400 Pa to about 5000 Pa, preferably in the range of from about 500 Pa to about 2000 Pa, more preferably in the range of from about 600 Pa to about 1500 Pa.

The injection force of the injectable soft tissue filler compositions of the present invention, measured through a needle of 27 G½ at a rate of 12.5 mm/min using a standard syringe, is usually between about 10 N and about 40 N, preferably between about 10 N and about 35 N, more preferably between about 15 N and about 30 N, and most preferably between about 20 N and about 25 N.

The osmolality is preferably from about 200 mOsmol/l to about 400 mOsmol/l, more preferably from about 280 mOsmol/l to about 330 mOsmol/l. In addition, since the injectable soft tissue filler compositions of the present invention are intended for insertion into the human body, the pH of the injectable soft tissue filler composition of the present invention is generally between about 6.5 and about 7.5, preferably between about 6.8 and about 7.4.

In a further aspect, the present invention relates to a fifth injectable soft tissue filler composition comprising a BDDE-crosslinked heparosan matrix and calcium hydroxyapatite.

The heparosan is preferably present in an amount of at least 0.1 wt. % or at least 0.5 wt. %, more preferably between about 0.1 wt. % and about 10.0 wt. % or between about 0.5 wt. % and about 4.0 wt. %, and most preferably between about 1.0 wt. % and about 3.0 wt. % or between about 1.5 wt. % and about 2.5 wt. %, based on the total weight of the fifth injectable soft tissue filler composition. Heparosan is usually the only crosslinked polymer in the injectable soft tissue filler composition. However, the fifth injectable soft tissue filler composition may further comprise non-crosslinked heparosan and/or non-crosslinked HA, preferably in amounts and having molecular weights as indicated above for other heparosan/HA containing compositions of the present invention.

The calcium hydroxyapatite particles are typically contained in the fifth injectable soft tissue filler composition in an amount of more than about 1 wt. %, preferably from about 10 wt. % to about 70 wt. %, more preferably from about 30 wt. % to about 60 wt. %, and most preferably from about 40 wt. % to about 50 wt. %.

The size of the calcium hydroxyapatite particles is preferably in the range of about 1 µm to about 1000 µm, more preferably in the range of about 10 µm to about 200 µm, particularly preferred in the range of about 20 µm to about 100 µm, and most preferably in the range of about 25 µm to about 50 µm. Furthermore, the ceramic particles have preferably a volume percent of about 5% to about 65%.

In addition, at least one active substance, for example one or more anesthetic agents, may be contained in the injectable soft tissue filler composition. The anesthetic agent is typically a local anesthetic such as lidocaine that is preferably comprised in the composition in a concentration as defined above in relation to other injectable soft tissue filler compositions of the present invention.

Moreover, the fifth injectable soft tissue filler composition of the present invention may optionally comprise one or more compounds selected from polyols, vitamins, amino acids, metals, minerals. Furthermore, the soft tissue filler of the present invention may also contain stem cells and/or growth factors and/or common additives (e.g. pH modifiers and osmolality adjusters). For a more detailed definition of these optional compounds, it is referred to the above definitions and explanations given in relation to other injectable soft tissue filler compositions of the present invention.

Preferably, the fifth injectable soft tissue filler composition further comprises glycerol and/or mannitol and/or lidocaine.

The fifth injectable soft tissue filler composition may have an elastic modulus G' at a crossover frequency (f) of 1 Hz of from about 400 Pa to about 5000 Pa, preferably from about 500 Pa to about 2000 Pa, more preferably from about 600 Pa to 1500 Pa. Furthermore, the injection force, as measured through a needle of 27 G½ at a rate of 12.5 mm/min using a standard syringe, is usually between about 10 N and about 40 N, preferably between about 10 N and about 35 N, more preferably between about 15 N and about 30 N, and most preferably between about 20 N and about 25 N. The osmolality is preferably from about 200 mOsmol/l to about 400 mOsmol/l, more preferably from about 280 mOsmol/l to about 330 mOsmol/l. The pH of the injectable soft tissue filler composition is usually about 6.5 to about 7.5, preferably about 6.8 to about 7.4.

Within the context of the present invention, the heparosan may also be a mixture of two or more heparosans that have different molecular weights. Preferably, the heparosan comprises a first heparosan having a first molecular weight of from about $0.5 \times 10^5$ Da to about $9.0 \times 10^5$ Da, more preferably from about $1.5 \times 10^5$ Da to about $5.0 \times 10^5$ Da, and a second heparosan having a second molecular weight of from about $1.0 \times 10^6$ Da to about $6.8 \times 10^6$ Da, more preferably from about $1.5 \times 10^6$ Da to about $5.0 \times 10^6$ Da.

In yet another aspect, the present invention relates to a kit comprising a syringe containing an injectable soft tissue filler of the present invention.

In a yet further aspect, the present invention relates to a process for the preparation of the first injectable soft tissue filler composition of the present invention, comprising the following steps:
  (a) providing an aqueous mixture comprising hyaluronic acid, heparosan, and 1,4-butanediol diglycidyl ether (BDDE),
  (b) crosslinking the mixture of (a) using BDDE as crosslinking agent, preferably under alkaline conditions, to obtain a hyaluronic acid-heparosan matrix.

Step (a) typically involves hydrating of pure, dry hyaluronic acid polymers and heparosan polymers in an alkaline solution. The hyaluronic acid referred to in step (a) is preferably sodium hyaluronate (NaHA). Said alkaline solution may be prepared by adding a desired amount of solid NaOH to the dry HA and heparosan polymers, followed by adding a suitable aqueous solvent, for example pure water, to hydrate the polymer mixture under alkaline conditions. In a variation of step (a), the crosslinker (i.e. BDDE) may also be present during hydration, i.e. present in the alkaline solution. Hydration of the polymers usually takes about 1 h to about 3 h and is preferably conducted under mixing.

In step (b), the mixture obtained in step (a) is BDDE-crosslinked. The crosslinking is generally carried out under alkaline conditions, typically in an alkaline aqueous solution. Suitable crosslinking techniques are well known to a skilled person and are not explained in detail herein. For example, the crosslinking may be started by the addition of an effective quantity of crosslinking agent and may be carried out at a temperature of from 20° C. to 60° C. (e.g., 50° C.). Preferably, the reaction mixture is mechanically homogenized prior to and/or during the crosslinking reaction. The crosslinking with BDDE leads to the formation of stable ether bonds which promotes stability of the produced gel under in vivo conditions.

The crosslinking reaction may be stopped by neutralization using an acid and/or elimination of the crosslinking agent during purification. The latter may, for example, be conducted by dialysis, which permits eliminating the crosslinking agent and short chains of polymer that have not reacted. The aqueous solution used for dialysis is generally a buffered solution. The composition of this buffer solution is selected so as to have the desired physico-chemical (pH, osmolarity) and rheological properties. Suitable buffer solutions include, but are not limited to, phosphate buffers, isotonic saline, and PBS buffers. After purification, the filler composition is usually filled in syringes, which are then sterilized by techniques known to those skilled in the art, for example by steam sterilization, autoclavation, and the like.

Furthermore, the present invention relates to a processes for the preparation of the second, third and fourth injectable soft tissue filler compositions of the present invention as disclosed herein above (see the Summary section) and in the appended claims. The techniques for preparing these compositions are well-known to those skilled in the art of manufacturing polysaccharide fillers. The reaction conditions described above also apply to the manufacturing of the second, third, fourth and fifth (see below) compositions. The crosslinking is generally stopped by carrying out dialysis. This eliminates the crosslinking agent, unreacted small polymer chains, undesired reaction products and other impurities. Generally, the soft tissue filler compositions of the present invention are sterile. To this end, the (first, second, third, fourth anf fifth) soft tissue filler compositions of the present invention may be filled into syringes and conveniently sterilized by autoclaving at, e.g., 121-132° C. for 2 to 30 min.

Moreover, the present invention relates to a process for the preparation of the fifth injectable soft tissue filler composition of the present invention, comprising step (A) of providing an aqueous mixture comprising heparosan, or one of its salts, and 1,4-butanediol diglycidyl ether (BDDE), step (B) of crosslinking the heparosan of using BDDE as crosslinking agent to obtain a crosslinked heparosan matrix, and step (C) of adding calcium hydroxyapatite. After step (B) and prior to step (C), the crosslinked heparosan matrix is purified to remove excess BDDE. Optionally, non-crosslinked HA or glycerol may be added as a lubricant.

In a yet further aspect, the present invention relates to the use of the injectable soft tissue filler compositions of the present invention, or of the kit of the present invention, for replacing or filling of a biological tissue or increasing the volume of a biological tissue in therapeutic or cosmetic applications. In particular, the present invention relates to a method for replacing or filling of a biological tissue or increasing the volume of a biological tissue, comprising administering to a subject in need thereof an effective amount of an injectable soft tissue filler composition of the present invention. The administration occurs generally by injection (e.g. subcutaneous or intradermal injection).

Preferably, the injectable soft tissue filler compositions of the present invention are administered only for cosmetic purposes (e.g., for improving the visual appearance, in particular of the face). In a particularly preferred embodiment, the injectable soft tissue filler compositions of the present invention are used as dermal filler that is intradermally or subcutaneously injected, such as by the serial puncture technique, into the target site (e.g. the tissue for which a volume increase (augmentation) is desired).

In particular, the injectable soft tissue filler compositions or the kit of the present invention may be used for therapeutic applications, such as for increasing the volume of the sphincter, the urethra or the vocal cords, or for applications in the (dermo)cosmetic field, such as for augmenting or filling of wrinkles or fine lines of the skin (e.g., nasolabial folds, marionette lines, chin folds, lower jawlines, oral commissure, and the like), filling cutaneous depressions, masking scars, increasing the volume of the lips, augmenting cheeks, nose corrections, and/or improve skin hydration and skin texture.

The present invention will now be further illustrated by the following, non-limiting examples.

EXAMPLES

The examples provided below illustrate the preparation of injectable soft tissue fillers of the present invention having good persistence in the human body, excellent biocompatibility, and desirable mechanical and rheological properties for use as a soft tissue filler.

Example 1

Preparation of a Single-Phase-Type HA Gel (Prior Art)

3.43 g of hyaluronic acid ($\eta$=0.6 m$^3$/kg; Mw=3.0×10$^5$ Da) are diluted in 13 ml of water for injection in order to hydrate the hyaluronic acid prior to crosslinking. After hydration for 16 hours, the mixture is homogenized until a transparent solution is obtained.

The crosslinking reaction is then started by the addition of 2.48 g of a 2 M NaOH solution, 5.74 g water for injection, and 390 mg of 1,4-butanediol diglycidyl ether (BDDE) to the reaction mixture, followed by mixing for 1 hour at 50° C. and crosslinking for 3 hours at 50° C. Next, the pH is adjusted to physiological pH with 1 M HCl, and the volume is diluted with 53.52 ml using a PBS buffer at pH 7.0.

The obtained gel is then dialyzed for 48 hours (limit of separation: $M_W$=12-14 kDa) against 35 liters of PBS buffer at pH 7.0. The resulting gel product has an adjusted total hyaluronic acid concentration of 25 mg/ml. The adjustment was done with PBS buffer at pH 7.0. Finally, the gel is sterilized by steam sterilization at 127° C. for 4 to 10 minutes. The resulting gel is referred to as "gel A" in the following.

Example 2

Preparation of a Single-Phase-Type Heparosan Gel (Prior Art)

3.68 g of heparosan ($M_W$=2.0×10$^5$ Da) are diluted in 12.77 ml of water for injection in order to hydrate the heparosan prior to crosslinking. After hydration for 16 hours, the mixture is homogenized until a transparent solution is obtained.

The crosslinking reaction is then started by the addition of 2.48 g of a 2 M NaOH solution, 5.73 g water for injection, and 390 mg of 1,4-butanediol diglycidyl ether (BDDE) to the reaction mixture, followed by mixing for 1 hour at 50° C. and crosslinking for 3 hours at 50° C. Next, the pH is adjusted to physiological pH with 1 M HCl, and the volume is diluted with 53.39 ml using a PBS buffer at pH 7.0.

The obtained gel is then dialyzed for 48 hours (limit of separation: $M_W$=12-14 kDa) against 35 liters of PBS buffer at pH 7.0. The resulting gel product has an adjusted total heparosan concentration of 25 mg/ml. The adjustment was done with PBS buffer at pH 7.0. Finally, the gel is sterilized by steam sterilization at 127° C. for 4 to 10 minutes. The resulting gel is referred to as "gel B" in the following.

Example 3

Preparation of a Heparosan/HA Soft Tissue Filler According to the Invention 1.71 g of hyaluronic acid ($\eta$=0.6 m$^3$/kg, $M_W$=3.0×10$^5$ Da) and 1.84 g heparosan ($M_W$=2.5×10$^5$ Da) are diluted in 12.88 ml water for injection in order to hydrate the hyaluronic acid and heparosan prior to crosslinking. After hydration for 16 hours, the mixture is homogenized until a transparent solution is obtained.

The crosslinking reaction is then started by the addition of 2.48 g of a 2 M NaOH solution, 5.71 g water for injection, and 390 mg of 1,4-butanediol diglycidyl ether (BDDE) to the reaction mixture, followed by mixing for 1 hour at 50° C. and crosslinking for 3 hours at 50° C. Next, the pH is adjusted to physiological pH with 1 M HCl, and the volume is diluted with 53.71 ml using a PBS buffer at pH 7.0.

The obtained gel is then dialyzed for 48 hours (limit of separation: $M_W$=12-14 kDa) against 35 liters of PBS buffer at pH 7.0. The resulting gel product has an adjusted total hyaluronic acid concentration of 12.5 mg/ml and a total heparosan concentration of 12.5 mg/ml, i.e. a total polymer concentration of 25.0 mg/ml. The adjustment was done with PBS buffer at pH 7.0. Finally, the gel is sterilized by steam sterilization at 127° C. for 4 to 10 minutes. The resulting gel is referred to as "gel C" in the following.

Example 4

Preparation of a Physical Mixture of a Crosslinked HA Gel and a Crosslinked Heparosan Gel According to the Invention First, a crosslinked HA gel was prepared according to Example 1 (gel A). Separately, a crosslinked heparosan gel was prepared according to Example 2 (gel B).

Next, the pre-formed crosslinked HA gel A was mixed with the pre-formed crosslinked heparosan gel B in a weight ratio of 1:1 by connecting a first 1 mL syringe containing gel A and a second 1 mL syringe containing gel B via a luer-lock adapter followed by manual mixing for 20 times back and forth. This physical mixture of gel A and gel B is referred to as "gel D" in the following.

Example 5

Preparation of a HEP Core+HA Shell Soft Tissue Filler According to the Invention 1.79 g of heparosan ("HEP"; $M_W$=2.0×10$^5$ Da) are diluted in 6.44 mL water for injection in order to hydrate the heparosan prior to crosslinking. After hydration for 16 hours, the mixture is homogenized until a transparent solution is obtained.

The crosslinking reaction is then started by the addition of 1.24 g of a 2M NaOH solution, 2.86 g water for injection, and 190 mg of 1,4-butanediol diglycidyl ether (BDDE) to the reaction mixture, followed by mixing for 1 hour at 50° C. and crosslinking for 1 hour at 50° C. to obtain a pre-crosslinked heparosan gel.

Separately, 1.79 g of hyaluronic acid ($\eta$=0.6 m$^3$/kg, $M_W$=3.0×10$^5$ Da) are diluted in 6.44 ml water for injection in order to hydrate the hyaluronic acid prior to crosslinking. After hydration for 16 hours, the mixture is homogenized until a transparent solution is obtained.

The obtained HA solution was then added to the pre-crosslinked heparosan gel obtained above, homogeneously mixed, and the crosslinking reaction was started by the addition of 1.24 g of a 2 M NaOH solution, 2.86 g water for injection, and 190 mg of 1,4-butanediol diglycidyl ether (BDDE) to the reaction mixture, followed by mixing for 10 minutes at 50° C. and crosslinking for 3 hours at 50° C. Next, the pH is adjusted to physiological pH with 1 M HCl, and the volume is diluted with 50.70 ml using a PBS buffer at pH 7.0.

The obtained gel is then dialyzed for 48 hours (limit of separation: $M_W$=12-14 kDa) against 35 liters of PBS buffer at pH 7.0. The resulting gel product has an adjusted total polymer concentration of 23.0 mg/ml (total heparosan concentration of 11.5 mg/ml and total HA concentration of 11.5 mg/ml). The adjustment was done with PBS buffer at pH 7.0. Finally, the gel is sterilized by steam sterilization at 127° C. for 4 to 10 minutes. The resulting gel is referred to as "gel E" in the following.

Example 6

Preparation of a HA Core+HEP Shell Soft Tissue Filler According to the Invention 1.79 g of hyaluronic acid ($\eta$=0.6 m$^3$/kg, $M_W$=3.0×10$^5$ Da) are diluted in 6.44 ml water for injection in order to hydrate the hyaluronic acid prior to crosslinking. After hydration for 16 hours, the mixture is homogenized until a transparent solution is obtained.

The crosslinking reaction is then started by the addition of 1.24 g of a 2 M NaOH solution, 2.86 g water for injection, and 190 mg of 1,4-butanediol diglycidyl ether (BDDE) to the reaction mixture, followed by mixing for 1 hour at 50° C. and crosslinking for 1 hour at 50° C. to obtain a pre-crosslinked HA gel.

Separately, 1.79 g of heparosan ("HEP", $M_W$=2.0×10$^5$ Da) are diluted in 6.44 ml water for injection in order to hydrate the heparosan prior to crosslinking. After hydration for 16 hours the mixture is homogenized until a transparent solution is obtained.

The obtained heparosan solution was then added to the pre-crosslinked HA gel obtained above, homogeneously mixed, and the crosslinking reaction was started by the addition of 1.24 g of a 2 M NaOH solution, 2.86 g water for injection, and 190 mg of 1,4-butanediol diglycidyl ether (BDDE) to the reaction mixture, followed by mixing for 10 minutes at 50° C. and 3 hours crosslinking at 50° C. Next, the pH is adjusted to physiological pH with 1 M HCl, and the volume is diluted with 51.49 ml using a PBS buffer at pH 7.0.

The obtained gel is then dialyzed for 48 hours (limit of separation: $M_W$=12-14 kDa) against 35 liters of PBS buffer at pH 7.0. The resulting gel product has an adjusted total polymer concentration of 23.0 mg/ml (total heparosan concentration of 11.5 mg/ml and total HA concentration of 11.5 mg/ml). The adjustment was done with PBS buffer at pH 7.0. Finally, the gel is sterilized by steam sterilization at 127° C. for 4 to 10 minutes. The resulting gel is referred to as "gel F" in the following.

Example 7

Comparison of Gels A-F Prepared in Examples 1-6

In this example, gels A-F as prepared in Examples 1-6 were characterized in terms of their extrusion force, elastic modulus (G') and viscous modulus (Tan δ), and their resistance against enzymatic degradation by hyaluronidase.

All rheological measurements were conducted using an Anton Paar MCR 302 Rheometer equipped with a cone of 1°, 50 mm diameter. The measurements were performed at a frequency (f) from 0.1 to 10 Hz with a constant gap of 0.1 mm. The injection force was measured through a needle of 30 G½ at a rate of 12.5 mm/min using a standard syringe.

In a first experiment, gels A to F were subjected to enzymatic degradation using 100 U hyaluronidase. The hyaluronidase treatment did not lead to any degradation of gel B (crosslinked heparosan), as indicated by a constant elastic modulus (G') over time (results not shown). However, gel C (crosslinked HEP+HA), gel E (HEP core+HA shell), and gel F (HA core+HEP shell) were found to be susceptible to enzymatic degradation. Notably, gel F was less prone to degradation than gels A, C, D, and E. Without being bound by any theory, this effect might be due to the presence of a less degradable HEP shell (or "coating") around a HA core. This is all the more remarkable as gel E with a opposite structure (HEP core+HA shell) was found to have a degradation profile similar to that of gel A (crosslinked HA).

In addition, gels A-F were subjected to rheological and extrusion force measurements. The results are shown in Table 1.

TABLE 1

Characteristics of gels A-F

| Characteristic | Gel A[1] | Gel B[2] | Gel C[3] | Gel D[4] | Gel E[5] | Gel F[6] |
|---|---|---|---|---|---|---|
| Extrusion force (N) | 62 | 31 | 15 | 20 | 32 | 27 |
| G' at 1 Hz (Pa) | 396 | 415 | 358 | 350 | 448 | 170 |
| Tan δ | 0.10 | 0.17 | 0.13 | 0.14 | 0.13 | 0.26 |

[1]= only crosslinked HA (cHA)
[2]= only crosslinked HEP (cHEP)
[3]= crosslinked HEP + HA
[4]= 1:1 mixture of gel A and gel B
[5]= HEP core + HA shell
[6]= HA core + HEP shell As can be seen from Table 1, gels C-F according to the present invention have low extrusion force values in the range of 15 to 32 N. In comparison, gel A, i.e. a crosslinked HA gel, has a significantly higher extrusion fore of 62 N. In addition, gels C-E have G' and Tan δ values that are in same range as those observed for gel A (cHA) and gel B (cHEP). Gel F has a lower G' and Tan δ as compared to gels C-E but exhibits a higher enzymatic degradation resistance (see above). Thus, the examples demonstrate that the gels according to the present invention can be easily extruded through fine needles while having desirable viscoelastic rheological properties (G' and Tan δ).

The invention claimed is:

1. An injectable soft tissue filler composition in the form of a gel, comprising heparosan and hyaluronic acid (HA), or one of their salts, crosslinked with 1,4-butanediol diglycidyl ether (BDDE) to form a crosslinked HA-heparosan matrix, wherein the heparosan has a molecular weight of from about $1.0 \times 10^5$ Da to about $6.8 \times 10^6$ Da, and wherein the injection force of the gel comprising the crosslinked HA-heparosan matrix is less than the injection force of a gel comprising the heparosan crosslinked with BDDE and/or a gel comprising the HA crosslinked with BDDE.

2. The injectable soft tissue filler composition of claim 1, wherein the weight ratio of heparosan to HA in said crosslinked HA-heparosan matrix is from about 1:99 to about 99:1.

3. The injectable soft tissue filler composition of claim 1, wherein the HA has a molecular weight of from about $1.0 \times 10^5$ Da to about $5.0 \times 10^6$ Da.

4. The injectable soft tissue filler composition of claim 1, further comprising non-crosslinked HA, wherein said non-crosslinked HA has a molecular weight of from about $3.0 \times 10^5$ Da to about $3.0 \times 10^6$ Da, and wherein the total amount of said non-crosslinked HA is from about 1 wt. % to about 50 wt. %, based on the total weight of the crosslinked and non-crosslinked heparosan and HA polymers present in the injectable soft tissue filler composition.

5. The injectable soft tissue filler composition of claim 1, further comprising non-crosslinked heparosan and non-crosslinked HA, wherein the total concentration of crosslinked and non-crosslinked heparosan and crosslinked and non-crosslinked HA polymers present in the injectable soft tissue filler composition is from about 10 mg/ml to about 35 mg/ml.

6. The injectable soft tissue filler composition of claim 1, wherein the injectable soft tissue filler composition contains no other non-crosslinked polymer other than non-crosslinked HA.

7. The injectable soft tissue filler composition of claim 1, wherein the composition further comprises particles having an average particle size of about 1 μm to about 1000 μm, wherein the particles are ceramic particles, and wherein the ceramic particles are contained in the injectable soft tissue filler composition in an amount of from about 5 wt. % to about 60 wt. %.

8. The injectable soft tissue filler composition of claim 1, wherein the injection force, measured through a needle of 27 G½ at a rate of 12.5 mm/min using a standard syringe, is from about 10 N to 30 N, and wherein the osmolality is in the range of about 200 mOsmol/l to about 400 mOsmol/l, and wherein the pH is between about 6.5 and about 7.5.

9. The injectable soft tissue filler composition of claim 1, wherein the weight ratio of heparosan to HA in said crosslinked HA-heparosan matrix is from about 50:50 to about 99:1.

10. The injectable soft tissue filler composition of claim 1, wherein the composition further comprises calcium hydroxyapatite particles, and further comprises lidocaine in an amount of from about 0.05 wt. % to about 5.0 wt. %, based on the total weight of the injectable soft tissue filler composition.

11. The injectable soft tissue filler composition of claim 1, wherein the crosslinked HA-heparosan matrix has a degree of modification, expressed as the ratio of the sum of mono- and double-linked BDDE-crosslinkers to the sum of HA and heparosan disaccharide units, of about 0.5% to about 25%.

12. The injectable soft tissue filler composition of claim 1, wherein the HA comprises a first HA having a first molecular weight in the range of from about $1.0 \times 10^5$ Da to less than about $1.0 \times 10^6$ Da and a second HA having a second molecular weight in the range of from about $1.0 \times 10^6$ Da to about $5.0 \times 10^6$ Da.

13. The injectable soft tissue filler composition of claim 1, wherein the heparosan comprises a first heparosan having a first molecular weight in the range of from about $1.0 \times 10^5$ Da and $9.0 \times 10^5$ Da and a second heparosan having a second molecular weight in the range of from about $1.0 \times 10^6$ to $3.0 \times 10^6$ Da.

14. The injectable soft tissue filler composition of claim 1, further comprising non-crosslinked heparosan, wherein said non-crosslinked heparosan has a molecular weight of from about $1.0 \times 10^5$ Da to about $6.8 \times 10^6$ Da, and wherein the total amount of said non-crosslinked heparosan is from about 1 wt. % to about 50 wt. %, based on the total weight of the crosslinked and non-crosslinked heparosan and HA polymers present in the injectable soft tissue filler composition.

15. The injectable soft tissue filler composition of claim 1, wherein the composition further comprises one or more polysaccharides other than HA and heparosan, in an amount of less than 10 wt. %, based on the total weight of all polysaccharides of the injectable soft tissue filler composition, said one or more other polysaccharides being selected, from the group consisting of chondroitin sulfate, keratan, keratan sulfate, heparin, heparin sulfate, cellulose and its derivatives, chitosan, carrageenan, xanthan, and alginate, or one of their salts.

16. The injectable soft tissue filler composition of claim 1, wherein the injectable soft tissue filler composition does not contain any non-crosslinked polymers.

17. The injectable soft tissue filler composition of claim 1, wherein the injectable soft tissue filler composition does not contain any non-crosslinked and crosslinked polymers other than HA and heparosan.

18. The injectable soft tissue filler composition of claim 1, wherein the composition further comprises at least one active substance.

19. The injectable soft tissue filler composition of claim 1, wherein the composition further comprises one or more compounds selected from the group consisting of polyols, vitamins, amino acids, metals, and minerals.

20. A kit comprising a syringe containing an injectable soft tissue filler according to claim 1.

21. A process for preparation of an injectable soft tissue filler composition according to claim 1, comprising:
   (a) providing an aqueous mixture comprising hyaluronic acid (HA), heparosan and 1,4-butanediol diglycidyl ether (BDDE), and
   (b) crosslinking the mixture of (a) using BDDE as crosslinking agent to obtain a crosslinked HA-heparosan matrix.

22. A method for replacing or filling of a biological tissue or increasing the volume of a biological tissue, comprising administering by injection to a subject in need thereof an effective amount of an injectable soft tissue filler composition according to claim 1.

* * * * *